(12) United States Patent
Onoda et al.

(10) Patent No.: US 8,430,999 B2
(45) Date of Patent: Apr. 30, 2013

(54) METHOD FOR DETECTING SAMPLE SUPPLY CONDITION, AND ANALYZER

(75) Inventors: Kazuteru Onoda, Kyoto (JP); Yoshiharu Sato, Kyoto (JP)

(73) Assignee: Arkray, Inc. (JP)

( * ) Notice: Subject to any disclaimer, the term of this patent is extended or adjusted under 35 U.S.C. 154(b) by 556 days.

(21) Appl. No.: 11/991,490

(22) PCT Filed: Aug. 29, 2006

(86) PCT No.: PCT/JP2006/316952
§ 371 (c)(1),
(2), (4) Date: Feb. 29, 2008

(87) PCT Pub. No.: WO2007/026683
PCT Pub. Date: Mar. 8, 2007

(65) Prior Publication Data
US 2009/0120806 A1    May 14, 2009

(30) Foreign Application Priority Data
Sep. 2, 2005    (JP) ................. 2005-255219

(51) Int. Cl.
*G01N 33/487*    (2006.01)
(52) U.S. Cl.
USPC ............ 204/403.01; 204/403.02; 204/403.03; 204/403.04; 204/403.05
(58) Field of Classification Search . 204/403.01–403.15
See application file for complete search history.

(56) References Cited

U.S. PATENT DOCUMENTS
6,790,327 B2 * 9/2004 Ikeda et al. ................ 204/403.1

6,875,327 B1    4/2005 Miyazaki et al.
2001/0006149 A1 * 7/2001 Taniike et al. ................ 204/403
(Continued)

FOREIGN PATENT DOCUMENTS
EP    1 369 684 A1    12/2003
JP    2001-208715    8/2001
(Continued)

OTHER PUBLICATIONS

International Search Report from the corresponding PCT/JP2006/316952, mailed Nov. 28, 2006.

(Continued)

*Primary Examiner* — Keith Hendricks
*Assistant Examiner* — Bach Dinh
(74) *Attorney, Agent, or Firm* — Studebaker & Brackett PC; Donald R. Studebaker

(57) ABSTRACT

The present invention relates to an analytical tool 1 which includes a flow path for moving a sample, and a working electrode 15 and a counter electrode 16 including active portions 15*c*, 16*c*, 16*d* for coming into contact with the sample supplied to the flow path and which is mounted in use to an analytical apparatus. The active portions 16*c*, 16*d* of the counter electrode 16 include a first active portion 16*c* and a second active portion 16*d* divided within the flow path. The working electrode 15 and the counter electrode 16 include contact ends 15*a*, 16*a* for coming into contact with terminals of an analytical apparatus when the analytical tool 1 is mounted to the analytical apparatus. At least one of the working electrode 15 and the counter electrode 16 includes a first electrode portion 16B which includes the contact end 16*a* and the first active portion 16*c* and a second electrode portion 16C which includes the second active portion 16*d*.

9 Claims, 12 Drawing Sheets

U.S. PATENT DOCUMENTS

| | | | |
|---|---|---|---|
| 2002/0189941 A1* | 12/2002 | Katsuki et al. | 204/403.01 |
| 2003/0159945 A1* | 8/2003 | Miyazaki et al. | 205/777.5 |
| 2003/0175946 A1* | 9/2003 | Tokunaga et al. | 435/287.2 |
| 2005/0000829 A1 | 1/2005 | Morita et al. | |
| 2006/0042941 A1* | 3/2006 | Kusaka et al. | 204/403.01 |
| 2006/0224658 A1 | 10/2006 | Sato et al. | |
| 2007/0131565 A1* | 6/2007 | Fujiwara et al. | 205/777.5 |

FOREIGN PATENT DOCUMENTS

| | | | |
|---|---|---|---|
| WO | WO 03/044514 | | 5/2003 |
| WO | WO 2004/011921 | | 2/2004 |
| WO | WO2004038397 | * | 5/2004 |
| WO | WO2005054840 | * | 6/2005 |

OTHER PUBLICATIONS

Supplementary European Search Report dated Aug. 24, 2011; Application No. EP 06 79 6932.

* cited by examiner

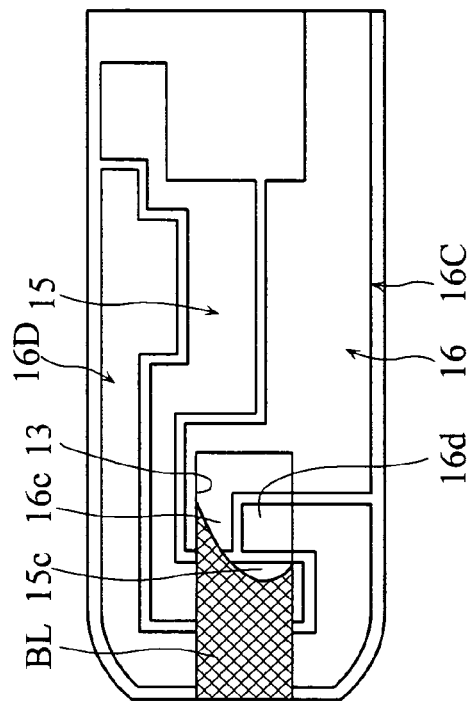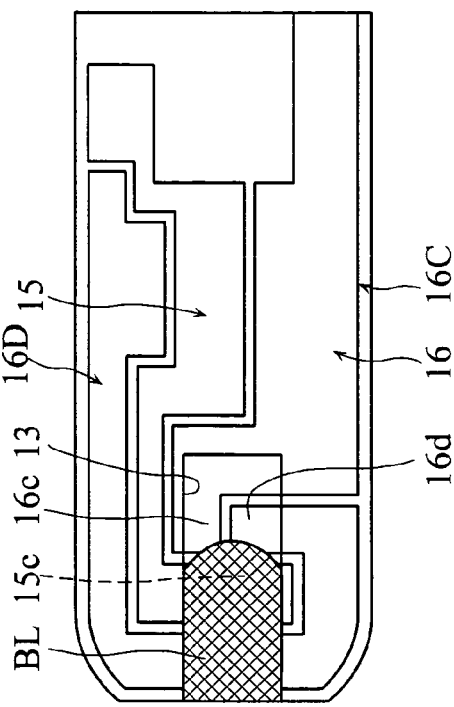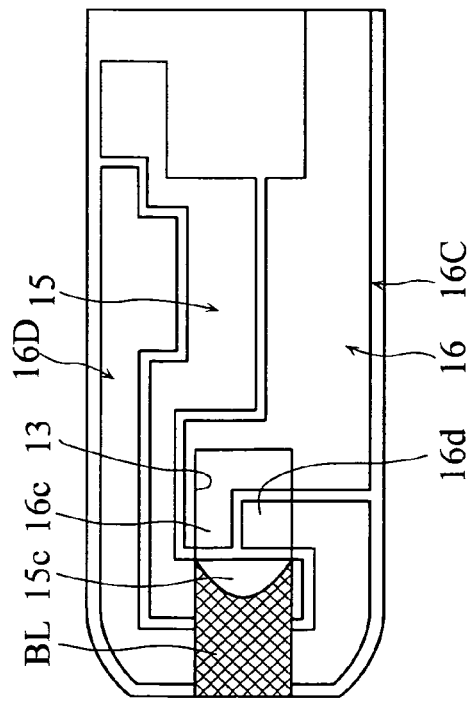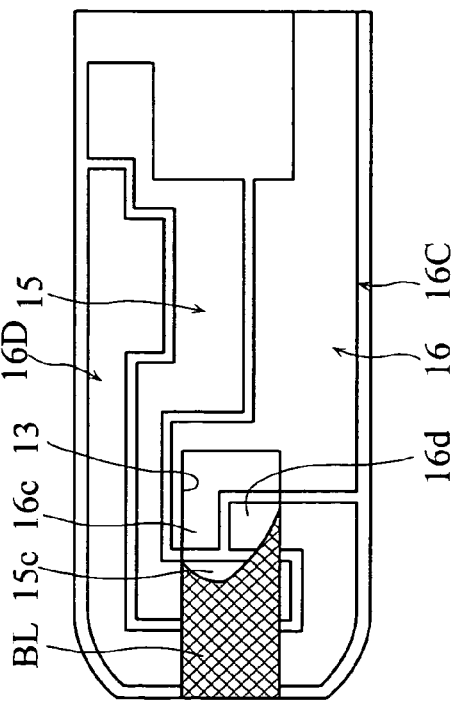

METHOD FOR DETECTING SAMPLE SUPPLY CONDITION, AND ANALYZER

TECHNICAL FIELD

The present invention relates to a technique to detect whether or not a sample is properly supplied to a flow path of an analytical tool such as a biosensor.

BACKGROUND ART

An analytical tool and an analytical apparatus are used in combination to analyze a particular component contained in a biochemical sample. For instance, to measure a glucose level (blood glucose level) contained in blood, a biosensor and a blood glucose level measuring apparatus are used in combination.

FIGS. 9-11 show a conventional biosensor. The biosensor 8 shown in the figures measures the blood glucose level by an electrochemical method and includes a substrate 80 to which a cover 82 is bonded via a spacer 81. The spacer 81 is formed with a slit 83, which defines a capillary 84 between the substrate 80 and the cover 82. A reagent layer 85 is provided in the capillary 84, so that a reaction field for reaction between blood and a reagent contained in the reagent layer 85 is provided when blood is introduced into the capillary. The substrate 80 is provided with a working electrode 86 and a counter electrode 87. The working electrode 86 and the counter electrode 87 are used for applying a voltage to the reaction field and measuring the response current obtained at the time.

To use the biosensor 8, such a blood glucose level measuring apparatus as shown in FIG. 12 is used. The blood glucose level measuring apparatus 9 shown in the figure includes connectors 90, 91 for coming into contact with the working electrode 86 or the counter electrode 87 and applying a voltage across the working electrode 86 and the counter electrode 87. The connector 90, which is to come into contact with the working electrode 86, is connected to a current-voltage conversion circuit 92 and an A/D conversion circuit 93. The connector 91, which is to come into contact with the counter electrode 87, is connected to ground.

The blood glucose level measuring apparatus 9 determines that blood is introduced into the capillary 84 when electrical connection between the working electrode 86 and the counter electrode 87 is detected and computes the blood glucose level based on the response current measured after the lapse of a predetermined period from the detection of the blood introduction.

As noted above, the blood glucose level measuring apparatus 9 determines that blood is introduced into the capillary 84 at the time point when electrical connection between the working electrode 86 and the counter electrode 87 is detected. Specifically, it is determined that blood is introduced into the capillary 84 when the response current exceeding a predetermined threshold is measured. Thus, in the blood glucose level measuring apparatus 9, the blood glucose level measurement is performed even when the amount of blood introduced into the capillary 84 is not sufficient for accurate measurement, though the blood is supplied. Thus, when the obtained blood glucose level is low, there is a possibility that the low value is caused by insufficient blood amount.

FIGS. 13 and 14 show another biosensor (see Patent Document 1, for example). In FIGS. 13 and 14, the elements which are identical or similar to those of the biosensor 8 shown in FIGS. 9-11 are designated by the same reference signs as those used for the biosensor 8.

The biosensor 8' further includes a detection electrode 88 in addition to the working electrode 86 and the counter electrode 87. The detection electrode 88 is utilized for determining whether or not blood is introduced into the capillary 84, and the portion of the detection electrode which is to come into contact with blood is provided on a downstream side in the blood flow direction (deeper side) in the capillary 84. Thus, the fact that the blood has reached the detection-electrode 88 means that the blood has reached both of the working electrode 86 and the counter electrode 87 and thus means that a sufficient amount of blood is introduced into the capillary 84.

To use the biosensor 8', such a blood glucose level measuring apparatus as shown in FIG. 15 is used. In FIG. 15, the elements which are identical or similar to those of the blood glucose level measuring apparatus 9 shown in FIG. 12 are designated by the same reference signs as those used for the blood glucose level measuring apparatus 9.

The blood glucose level measuring apparatus 9' further includes a connector 94 for coming into contact with the detection electrode 88 in addition to the connectors 90 and 91. The connector 94 is connected to ground. Specifically, by opening or closing the switch 96 by a CPU 95, the connector 91 is connected to ground or not connected to ground.

The blood glucose level measuring apparatus 9' determines that blood is introduced into the capillary 84 when electrical connection between the detection electrode 88 and the working electrode 86 is detected, with the switch 96 closed. Further, with the switch 96 opened, the blood glucose level measuring apparatus 9' applies a voltage across the working electrode 86 and the counter electrode 87 via connectors 90, 91 and measures the response current obtained at the time. The blood glucose level is computed based on the response current measured after the lapse of a predetermined period from the detection of the blood introduction.

As noted above, the biosensor 8' includes a detection electrode 88, and the portion of the detection electrode 88 which is to come into contact with blood is provided on a deeper side relative to the portion of the working electrode 86 and the counter electrode 87 which is to come into contact with blood. Thus, the determination that blood is introduced into the capillary 84 is made only when the amount of the blood introduced into the capillary 84 is sufficient.

However, the provision of the detection electrode 88 for detecting blood introduction into the capillary 84 in addition to the working electrode 86 and the counter electrode 87 increases the manufacturing cost of the biosensor 8'.

Further, the blood glucose level measuring apparatus 9' used for the biosensor 8' requires the additional connector 94 for the detection electrode 88. Moreover, it is also necessary to provide the switch 96 for selecting the state in which the connector 94 is connected to ground or the state in which the connector is not connected to ground and to control the on/off operation of the switch 96. Thus, as compared with the blood glucose level measuring apparatus 9 (see FIG. 12) used for the biosensor 8 (see FIGS. 9-12) which does not include a detection electrode 88, this blood glucose level measuring apparatus has a complicated structure and needs various control. Thus, the manufacturing cost of the blood glucose level measuring apparatus 9' is higher than that of the blood glucose level measuring apparatus 9 (see FIG. 12).

Patent Document 1: JP-A-2001-208715

DISCLOSURE OF THE INVENTION

Problems to be Solved by the Invention

An object of the present invention is to reliably detect the lack of sample supply to a capillary of an analytical tool to prevent incorrect measurements due to the sample lack while preventing an increase in the manufacturing cost of an analytical tool and an analytical apparatus by employing a simple structure.

Means for Solving the Problems

According to a first aspect of the present invention, there is provided a sample supply detection method for detecting, in sample analysis using an analytical tool including a flow path for moving a sample, whether or not a necessary amount of sample is supplied to the flow path. The analytical tool further includes a working electrode and a counter electrode for applying a voltage to the sample supplied to the flow path and measuring detection current detected during the voltage application. The method comprises a first step of determining whether or not the detection current has exceeded a predetermined threshold, and a second step of determining whether or not a peak appears in a time course of the detection current before lapse of a predetermined period from when the detection current exceeded the threshold. The second step is performed in the case where it is determined in the first step that the detection current has exceeded the threshold. The method further comprises a third step of determining whether or not the detection current monotonically decreases after the peak detection in the case where the peak is detected in the second step, and a fourth step of determining whether or not a necessary amount of sample is properly supplied to the flow path based on the determination in the first through the third steps.

For instance, when the peak is not detected in the second step before the lapse of a predetermined period after it is determined that the detection current has exceeded the threshold, it may be determined in the fourth step that the amount of sample necessary for analysis is not properly supplied to the flow path.

When it is determined in the third step that the detection current after the peak detection does not monotonically decrease before the lapse of the predetermined period after it is determined that the detection current has exceeded the threshold, it may be determined in the fourth step that the amount of sample necessary for analysis is not properly supplied to the flow path.

When the peak is detected in the second step before the lapse of the predetermined period after it is determined in the first step that the detection current has exceeded the threshold and it is determined in the third step that the detection current after the peak detection monotonically decreases, it may be determined in the fourth step that the amount of sample necessary for analysis is properly supplied to the flow path.

For instance, the predetermined period may be selected from the ranges of 0.1 seconds to 3.0 seconds.

For instance, the time course of the detection current is obtained based on a plurality of detection current values measured at predetermined time intervals. In this case, the time interval is selected from the ranges of 25 to 200 msec.

For instance, in the analytical tool used for the sample supply detection method according to the present invention, at least one of the working electrode and the counter electrode includes an active portion for coming into contact with the sample, and the active portion of at least one of the working electrode and the counter electrode includes a first active portion and a second active portion divided within the flow path.

According to a second aspect of the present invention, there is provided an analytical tool comprising a flow path for moving a sample, and a working electrode and a counter electrode for applying a voltage to the sample supplied to the flow path. Each of the working electrode and the counter electrode includes an active portion for coming into contact with the sample, and the analytical tool is mounted in use to an analytical apparatus. The active portion of at least one of the working electrode and the counter electrode includes a first active portion and a second active portion divided within the flow path.

For instance, in the analytical tool according to the first and the second aspects of the present invention, each of the working electrode and the counter electrode may include a contact end for coming into contact with a terminal of an analytical apparatus when the analytical tool is mounted to the analytical apparatus. In this case, at least one of the working electrode and the counter electrode includes a first electrode portion which includes the contact end and the first active portion and a second electrode portion which includes the second active portion.

For instance, the first active portion and the second active portion may be arranged along a direction crossing the sample flow direction in the flow path. Alternatively, the first active portion and the second active portion may be arranged along the sample flow direction in the flow path or divided along both of the sample flow direction in the flow path and the direction crossing the sample flow direction or arranged in other ways.

The counter electrode may include an additional active portion for coming into contact with the sample, and the additional active portion may be connected to the second active portion. In this case, the additional active portion, the active portion of the working electrode and the active portion of the counter electrode are arranged in the mentioned order along the sample flow direction in the flow path.

The analytical tool according to the present invention may further include a reagent layer containing e.g. an electron mediator. The reagent layer may be arranged to continuously covering the active portion of the working electrode and the active portion of the counter electrode. When the additional active portion, the active portion of the working electrode and the active portion of the counter electrode are arranged along the sample flow direction, the reagent layer may be so arranged as to continuously cover these active portions.

For instance, the flow path may be configured to move the sample by capillary action.

BRIEF DESCRIPTION OF THE DRAWINGS

FIG. 4 includes a schematic view of the biosensor of FIG. 1 in a state in which the amount of blood introduced into the capillary is insufficient.

BEST MODE FOR CARRYING OUT THE INVENTION

A biosensor as an example of analytical tool according to the present invention and a method for detecting blood supply lack by using the biosensor and a blood glucose level measuring apparatus will be described below with reference to the accompanying drawings.

Figure 1:
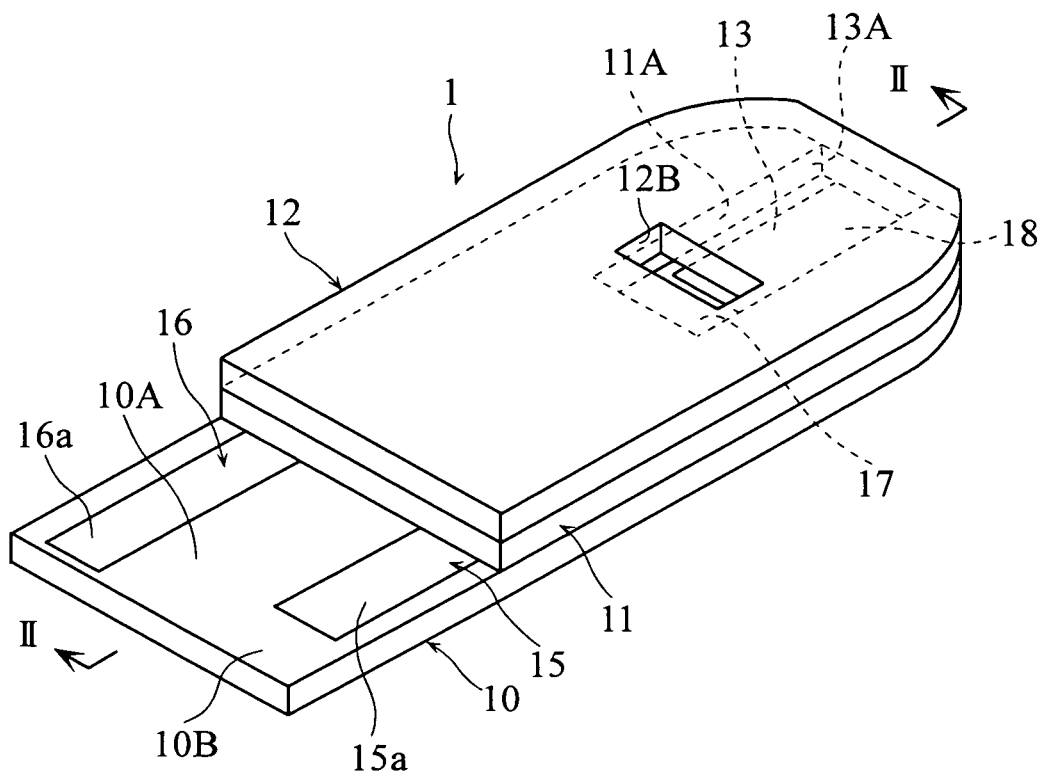
FIG. 1 is an overall perspective view showing a biosensor as an example of analytical tool according to the present invention.
Figure 2:
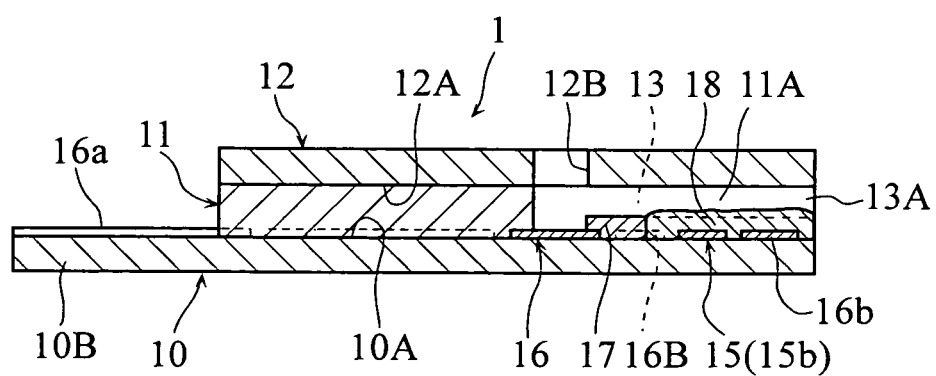
FIG. 2 is a sectional view taken along lines II-II in FIG. 1.
Figure 3:
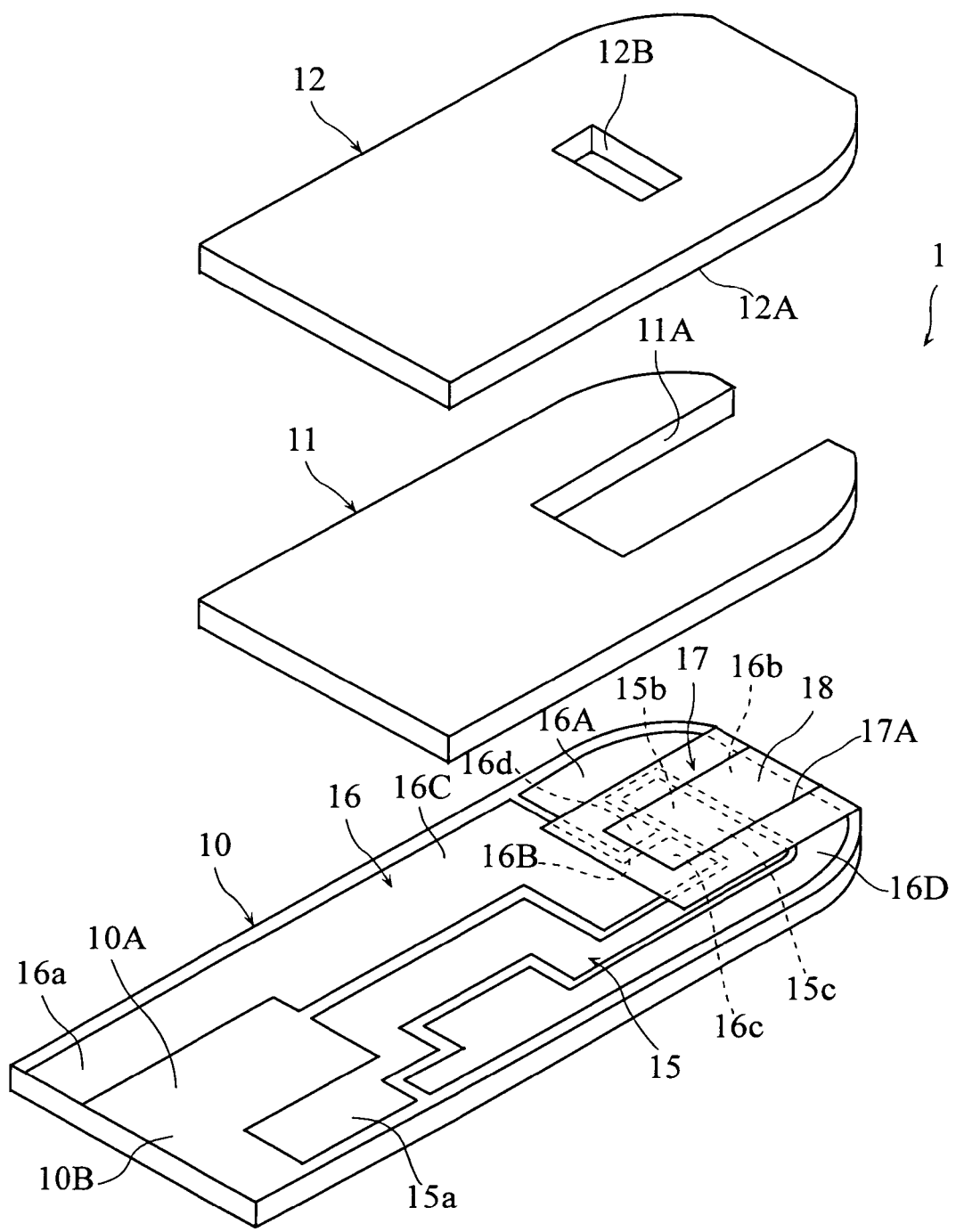
FIG. 3 is an exploded perspective view of the biosensor shown in FIG. 1.
Figure 5:
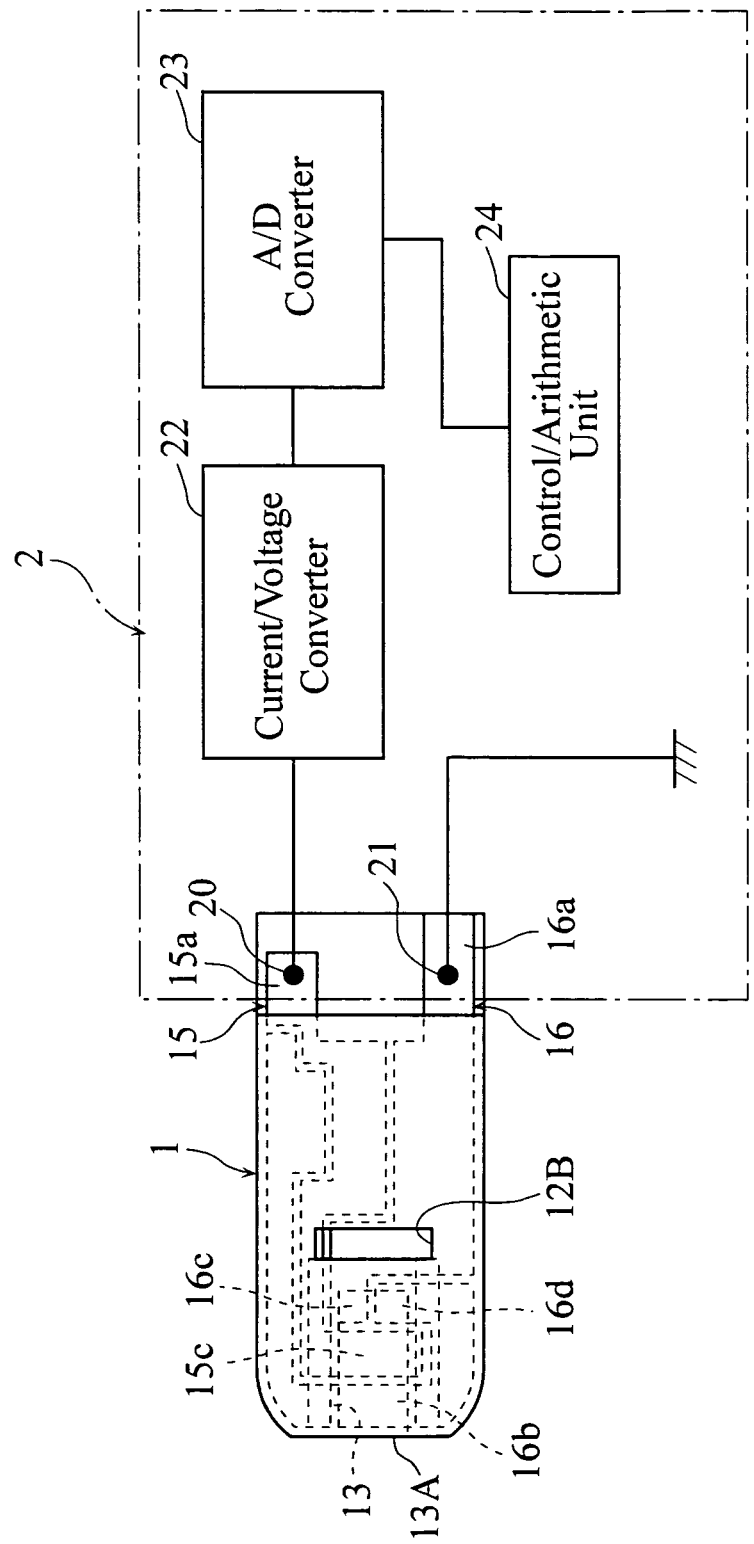
FIG. 5 shows a biosensor mounted to a blood glucose level measuring apparatus according to the present invention, in which the analytical apparatus is illustrated in a block diagram, whereas the biosensor is illustrated in a plan view.

The biosensor 1 shown in FIGS. 1-3 is a disposable one which is mounted in use to a blood glucose level measuring apparatus 2 (see FIG. 5). The biosensor 1 includes a substrate 10 which is generally in the form of an elongated rectangle and a cover 12 bonded to the substrate via a spacer 11. These elements 10-12 define a capillary 13 extending in the longitudinal direction of the substrate 10 in the biosensor 1.

The spacer 11 defines the distance from the upper surface 10A of the substrate 10 to the lower surface 12A of the cover 12, i.e., the height of the capillary 13 and may comprise a double-sided tape. The spacer 11 is formed with a slit 11A having an open end. The slit 11A defines the width of the capillary 13. The open end of the slit 11A provides an introduction port 13A for introducing blood into the capillary 13.

The cover 12 is formed with an exhaust port 12B for discharging gas from the capillary 13. The cover 12 is made of a thermoplastic resin having a high wettability such as Vinyl on or highly crystalline PVA, for example.

The substrate 10 is made of an insulating resin material such as PET and is made larger than the cover 12. The substrate 10 includes an end 10B projecting sideways of the cover 12. The upper surface 10A of the substrate 10 is formed with a working electrode 15, a counter electrode 16, an insulating mask 17 and a reagent layer 18.

The working electrode 15 and the counter electrode 16 are used for applying a voltage to the blood introduced into the capillary 13 and respectively include ends 15a and 16a which are not covered by the cover 12 and exposed at the end 10B of the substrate 10. When the biosensor 1 is mounted to the blood glucose level measuring apparatus 2, the ends 15a and 16a come into contact with terminals 20 and 21 (see FIG. 5) of the blood glucose level measuring apparatus 2.

The working electrode 15 further includes an end 15b which extends in the widthwise direction of the substrate 10 and part of which is positioned within the capillary 13.

The counter electrode 16 includes an S-shaped bent portion 16A. The bent portion 16A surrounds the end 15b of the working electrode 15. The counter electrode 16 is divided at the bent portion 16A in the capillary 13 by a slit 16B extending in the longitudinal direction of the substrate 10 (the direction of blood movement in the capillary 13). Thus, the counter electrode 16 is made up of a first portion 16C including the end 16a, and a second portion 16D, i.e., the portion other than the first portion, which includes the portion surrounding the end 15b of the working electrode 15.

The working electrode 15 and the counter electrode 16 can be formed simultaneously by screen printing using a conductive carbon ink.

The insulating mask 17 prevents the working electrode 15 and the counter electrode 16 from short-circuiting and includes a slit 17A. The slit 17A exposes intended portions of the working electrode 15 and the counter electrode 16 within the capillary 13 and defines a region for providing the reagent layer 18. In the slit 17A, portions of the working electrode 15 and the counter electrode 16 which are in contact with the reagent layer 18 provide active portions 15c, 16b, 16c, 16d. The active portion 16b, the active portion 15c, and the active portions 16c and 16d are arranged in the blood flow direction in the mentioned order. The active portions 16c and 16d of the counter electrode 16 substantially serve as a detection electrode.

The insulating mask 17 is not limited to the illustrated example and may have another shape as long as it includes an opening for providing the reagent layer 18. For instance, the opening may have a shape other than the slit. The insulating mask may have a shape which is similar to the cover 11 in plan view (i.e., the structure covering the portions other than the ends 15a, 16a and the active portions 15c, 16b, 16c, 16d of the working electrode 15 and the counter electrode 16).

The reagent layer 18 is arranged in the slit 17A of the insulating mask 17 to continuously cover the active portions 15c, 16b, 16c, 16d of the working electrode 15 and the counter electrode 16. The reagent layer 18 may contain an electron mediator and an oxidoreductase. The reagent layer 18 is in a porous solid state which easily dissolves in blood.

As the electron mediator, use may be made of a ruthenium complex or an iron complex, and $[Ru(NH_3)_6]Cl_3$ or $K_3[Fe(CN)_6]$ may be typically used. As the oxidoreductase, use may be made of glucose oxidase (GOD) or glucose dehydrogenase (GDH), and PQQGDH may be typically used.

The regent layer does not necessarily need to continuously cover the active portions 15c, 16b, 16c, 16d of the working electrode 15 and the counter electrode 16. For instance, a plurality of separate reagent layers such as a first reagent layer which covers the active portions 15c, 16b and a second reagent layer which is provided separately from the first reagent layer and covers the active portions 16c, 16d may be provided. In the case where a plurality of reagent layers are provided, the reagent layers may contain different reagents.

The capillary 13 is utilized for moving the blood introduced from the introduction port 13A in the longitudinal direction of the substrate 10 by capillary action and retaining the introduced blood. Specifically, when blood is introduced into the capillary 13 through the introduction port 13A, the blood moves while discharging gas from the capillary 13 through the exhaust port 12B. In this process, the reagent layer 18 in the capillary 13 is dissolved to establish a liquid phase reaction system containing electron mediator, oxidoreductase and glucose. The movement of the blood in the capillary 13 is stopped when the blood reaches an edge of the exhaust port 12B.

Figure 6:
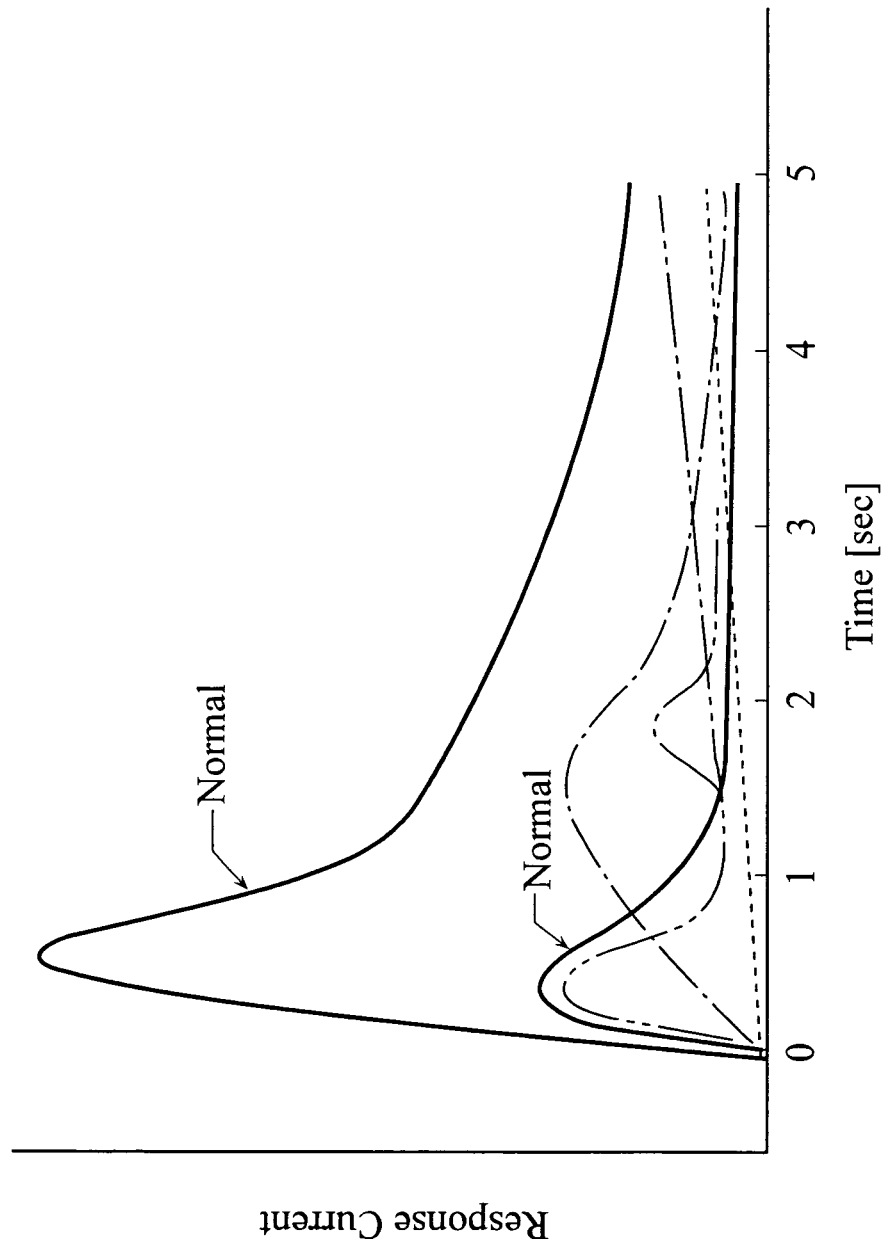
FIG. 6 is a graph showing time courses of response current measured in the blood glucose level measuring apparatus shown in FIG. 5.

FIGS. 4A and 4B show the case in which the amount of blood BL introduced into the capillary 13 is insufficient and the active portion 15c of the working electrode 15 and the active portion 16c of the first portion 16C of the counter electrode 16 are not electrically connected to each other via the blood BL. In this case, electric current does not flow in the biosensor 1. FIG. 4C shows the case in which the active portion 15c of the working electrode 15 and the active portion 16c of the first portion 16C of the counter electrode 16 are electrically connected to each other via the blood BL, but the active portion 16d of the second portion 16D of the counter electrode 16 and the active portion 15c of the working electrode 15 are not electrically connected via the blood (i.e., the active portion 16c of the first portion 16C and the active portion 16d of the second portion 16D of the counter electrode 16 are not electrically connected to each other). FIG. 4D shows the case in which the active portion 16c of the first portion 16C and the active portion 16d of the second portion 16D of the counter electrode 16 are electrically connected to each other only at portions thereof. In the cases shown in FIGS. 4C and 4D, although, the liquid junction current flows, the current is extremely weak or flows in a manner different from the normal state (as indicated by the chain line, the single-dashed line and the double-dashed line in FIG. 6), because the counter electrode 16 is divided within the capillary 13. Thus, even when the working electrode 15 and the counter electrode 16 are electrically connected to each other via the blood in the biosensor 1, the behavior of the current differs greatly between the case in which the amount of the blood introduced into the capillary 13 is sufficient and the case in which the amount of the blood introduced into the capillary 13 is insufficient.

The blood glucose level measuring apparatus 2 shown in FIG. 5 is an apparatus for measuring the glucose level (blood glucose level) of the blood supplied to the biosensor 1 and includes terminals 20 and 21, a current-voltage conversion circuit 22, an A/D conversion circuit 23 and a control/arithmetic circuit 24.

The terminals 20 and 21 are portions to come into contact with the ends 15a and 16a of the working electrode 15 and the counter electrode 16 of the biosensor 1 and used for forming a potential difference between the working electrode 15 and the counter electrode 16. The terminal 20 is connected to the current-voltage conversion circuit 22, whereas the terminal 21 is connected to ground.

The current-voltage conversion circuit 22 converts current to voltage (analog signals) for outputting and is connected to the terminal 20 and the A/D conversion circuit 23.

The A/D conversion circuit 23 converts the analog signals outputted from the current-voltage conversion circuit 22 into digital signals for outputting and is connected to the current-voltage conversion circuit 22 and the control/arithmetic circuit 24.

The control/arithmetic circuit 24 controls various elements and determines whether or not blood is introduced into the capillary 13 and whether or not the amount of the blood introduced into the capillary 13 is sufficient or computes the blood glucose level based on the digital signals outputted from the A/D conversion circuit 23. The control/arithmetic circuit 24 may comprise a CPU, a RAM and a ROM.

The measurement of a blood glucose level using the biosensor 1 and the blood glucose level measuring apparatus 2 will be described below.

The blood glucose level measurement is performed automatically in the blood glucose level measuring apparatus 2 when the biosensor 1 is mounted to the blood glucose level measuring apparatus 2 and blood is supplied to the biosensor 1.

Specifically, when the biosensor 1 is mounted to the blood glucose level measuring apparatus 2, the ends 15a, 16a of the working electrode 15 and the counter electrode 16 of the biosensor 1 come into contact with the terminals 20, 21 of the blood glucose level measuring apparatus 2. The blood introduced into the capillary 13 of the biosensor 1 through the introduction port 13A moves toward the exhaust port 12B due to the capillary action which occurs in the capillary 13. When an appropriate amount of blood is introduced into the capillary 13, the reagent layer 18 is quickly dissolved by the blood, whereby a liquid phase reaction system is established in the capillary 13. For instance, in the liquid phase reaction system, oxidoreductase reacts specifically with glucose in the blood to take electrons from glucose, and the electrons are transferred to the electron mediator, whereby the electron mediator becomes the reduced form.

In the blood glucose level measuring apparatus 2, a potential difference is formed between the terminals 20 and 21, so that a potential difference is formed between the working electrode 15 and the counter electrode 16. When the blood reaches the active portion 16c of the first portion 16C of the counter electrode 16 and the active portion 16c and the active portion 15c of the working electrode 15 are electrically connected to each other, current flows between the working electrode 15 and the counter electrode 16. The current is converted into voltage at the current-voltage conversion circuit 22 to be inputted into the A/D conversion circuit 23 and then outputted from the A/D conversion circuit 23 as a digital signal corresponding to the level of the current. The digital signal is inputted into the control/arithmetic circuit 24. When a potential difference is formed between the working electrode 15 and the counter electrode 16 with a liquid phase reaction system established, electrons are transferred from the electron mediator in the reduced form to the active portion 15c of the working electrode 15. The amount of the electrons transferred to the active portion 15c of the working electrode 15 is grasped as a response current at predetermined time intervals (e.g. intervals of 50 msec) finally as related to the level of the digital signal inputted into the control/arithmetic circuit 24.

When a sufficient amount of blood is introduced into the capillary 13 of the biosensor 1 (in the normal state), the blood reaches the active portions 16c, 16d of the first portion 16C of the counter electrode 16 immediately after the introduction. As a result, the active portions 16c, 16d and the active portion 15c of the working electrode 15 are electrically connected to each other, and the regent layer 18 dissolves quickly. Thus, in the normal state, the time course of the digital signals (magnitude of the response current) inputted into the control/arithmetic circuit 24 is like that indicated by the solid lines in FIG. 6. Specifically, the response current reaches the peak immediately after the blood is introduced into the capillary 13 and then decreases monotonically. In the figure, the solid line with a relatively high peak indicates the time course in the case where the blood glucose level is at a medium or high level, whereas the solid line with a relatively low peak indicates the time course in the case where the blood glucose level is at a low level.

When the amount of the blood introduced into the capillary 13 is insufficient, the time course of the response current is like that schematically indicated by the chain line, the single-dashed line and the double-dashed line in the figure. Specifically, when the amount of blood is insufficient, the blood does not reach the entirety of the active portions 16c, 16d of the first portion 16B of the counter electrode 16 immediately after the blood is introduced (see FIGS. 4A-4D, for example), and the reagent layer 18 does not dissolve quickly. Thus, when the blood introduced into the capillary 13 is insufficient, the response current monotonically increases within a low range as schematically indicated by the chain line in the figure or reaches the peak later than in the normal state as schematically indicated by the single-dashed line in the figure. Alternatively, as schematically indicated by the double-dashed line in the figure, although the response current reaches the peak at a similar timing to the normal state, the response current does not decrease monotonically after the peak, i.e., the response current starts to increase monotonically or reaches another peak after a certain period from the peak. Though not illustrated, in the case where the response current does not decrease monotonically after the first peak, the response current may fluctuate after the first peak.

The control/arithmetic circuit 24 successively grasps the level of the inputted digital signal (magnitude of the current) at predetermined time intervals and determines whether or not the level is higher than a predetermined threshold. For instance, the threshold may be set to a value corresponding to the current that flows when the active portion 16c of the first portion 16C and the active portion 16d of the second portion 16D of the counter electrode 16 are properly connected to each other electrically. When the level of the inputted digital signal is determined to be higher than the predetermined threshold, the control/arithmetic circuit 24 sets the point of the determination as a zero point and grasps the level of the inputted digital signal at predetermined time intervals (e.g. intervals of 200 msec).

After setting the zero point, the control/arithmetic circuit 24 determines whether or not a sufficient amount of blood is supplied to the capillary 13 based on the digital signals obtained successively. This determination process includes a peak detection step of determining whether or not the peak of the time course appears after the lapse of a predetermined period (e.g. 0.1 to 3.0 seconds) from the zero point, a monotonic decrease detection step of determining whether or not the response current monotonically decreases after the peak in the case where the peak is detected in the peak detection step, and a determination step of determining whether or not a sufficient amount of blood is supplied to the capillary 13 based on the determination results of the peak detection step and the monotonic decrease detection step.

When the peak of the time course is not detected before the lapse of the predetermined period from the zero point in the peak detection step, the control/arithmetic circuit 24 determines in the determination step that a sufficient amount of blood is not supplied to the capillary 13. Owing to such determination, when the amount of blood is insufficient so that the time course of the response current is like that schematically indicated by the chain line or the single-dashed line in FIG. 6, the fact that a sufficient amount of blood is not supplied to the capillary 13 is properly detected.

Further, when the peak is detected in the peak detection step and the fact that the response current does not monotonically decrease after the peak, the control/arithmetic circuit 24 determines in the determination step that a sufficient amount of blood is not supplied to the capillary 13. Owing to such determination, when the amount of blood is insufficient so that the time course of the response current is like that schematically indicated by the double-dashed line or the response current fluctuates after the peak, the fact that a sufficient amount of blood is not supplied to the capillary 13 is properly detected.

When it is determined that a sufficient amount of blood is not supplied to the capillary 13, the control/arithmetic circuit 24 performs error handling without performing the computation of the blood glucose level and finishes the blood glucose level measurement process. The fact that error handling is performed is displayed at e.g. a display panel (not shown) of the blood glucose level measuring apparatus 2.

When the peak of the time course is detected before the lapse of the predetermined period from the zero point in the peak detection step and monotonic decrease of the response current is observed after the peak, the control/arithmetic circuit 24 determines that a sufficient amount of blood is supplied to the capillary 13 and proceeds the blood glucose level measurement. Specifically, the control/arithmetic circuit 24 samples the response current value (level of the digital signal from the A/D conversion circuit 23) measured when a predetermined period (e.g. five seconds) has lapsed from the time point at which the blood introduction into the capillary 13 is detected (i.e. zero point) and applies the sampled response current value to a calibration curve prepared in advance. Thus, the blood glucose level is computed. The result of the blood glucose level computation is displayed at e.g. a display panel (not shown) of the blood glucose level measuring apparatus 2.

According to the present invention, the counter electrode 16 of the biosensor 1 is divided within the capillary 13, as described above. Thus, even when the working electrode 15 and the counter electrode 16 are electrically connected to each other via blood, the magnitude of the measured current differs greatly between when the amount of the blood introduced into the capillary 13 is sufficient and when the blood is insufficient. Thus, the lack of the amount of the blood introduced into the capillary 13 is reliably detected. Further, since the active portions 16c, 16d of the counter electrode 16, which substantially function as detection electrodes, are provided downstream in the blood flow direction from the active portion 16b of the counter electrode 16 and the active portion 15c of the working electrode 15, the fact that the blood has reached the active portion 16b of the counter electrode 16 and the active portion 15c of the working electrode 15 is reliably detected. These advantages of the biosensor 1 are obtained just by devising the shape of the counter electrode 16 and dividing the counter electrode 16 without providing an additional detection electrode like that provided in the conventional structure. Thus, in the biosensor 1, the introduction of blood into the capillary 13 is reliably detected without increasing the manufacturing cost.

Further, in the present invention, whether or not the amount of the blood introduced into the capillary 13 is sufficient is determined by grasping the time course of the response current and checking the presence or absence of the peak of the time course or the behavior of the response current after the peak (i.e., whether or not the response current monotonically decreases) if the peak exists. Thus, the lack of the amount of the blood introduced into the capillary 13 is reliably detected. Since the biosensor 1 does not include a detection electrode, this advantage of the blood glucose level measuring apparatus 2 is obtained without the need for providing a terminal or a switch for a detection electrode and controlling the on/off operation of a switch. Thus, in the blood glucose level measuring apparatus 2, the introduction of blood into the capillary 13 is reliably detected without increasing the manufacturing cost.

As described above, according to the present invention, the lack of the amount of the blood introduced into the capillary 13 is reliably detected with an inexpensive structure by devising the shape of the counter electrode 16 of the biosensor 1 and devising the data processing of the response current obtained in the blood glucose level measuring apparatus 2. Thus, the situation in which the amount of the blood introduced into the capillary 13 is so insufficient that an unduly low measurement value will be obtained if measurement is performed is properly handled as an error. Further, the situation in which the blood glucose level is actually low is properly distinguished from the situation in which the amount of the blood introduced is insufficient. Thus, the reliability of the measurement of a low blood glucose level is enhanced.

Figure 7A:
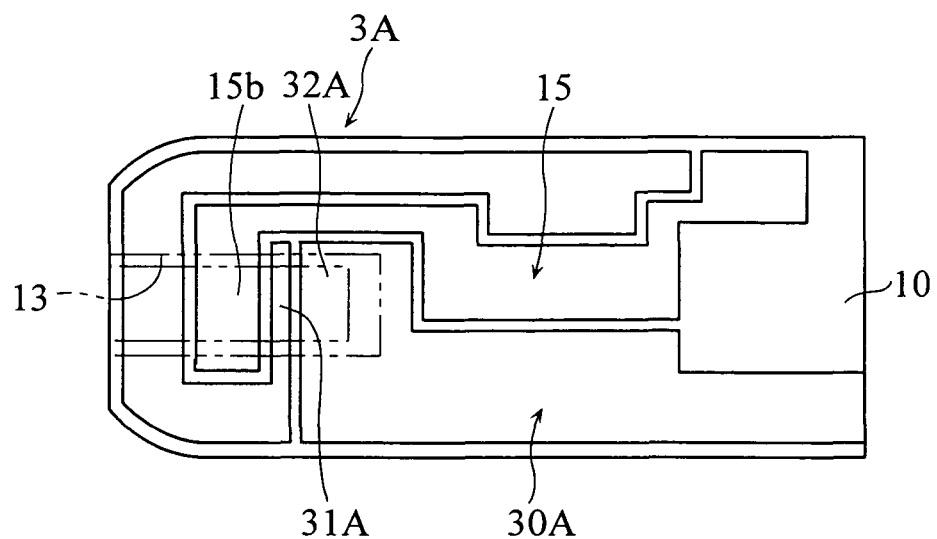
FIG. 7 includes a plan view showing other examples of biosensor according to the present invention in a state in which a cover and a spacer are removed.
Figure 7B:
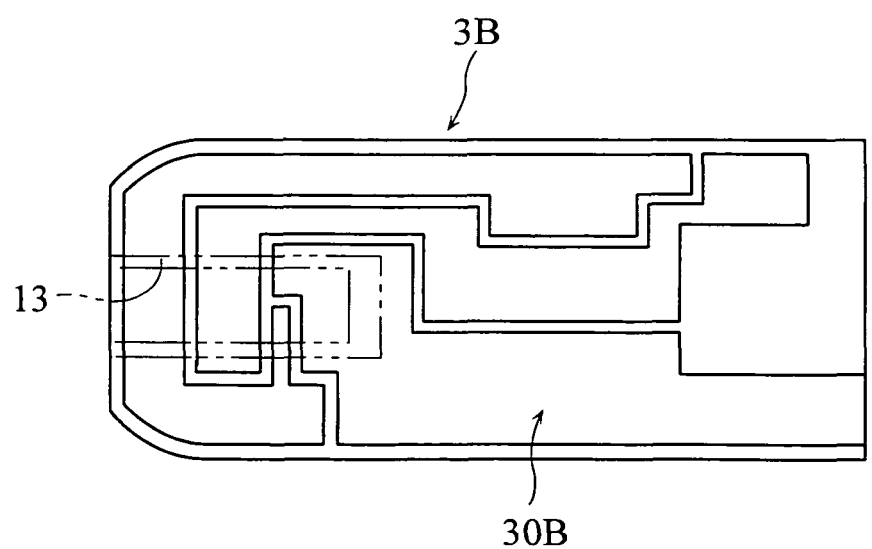
Figure 8A:
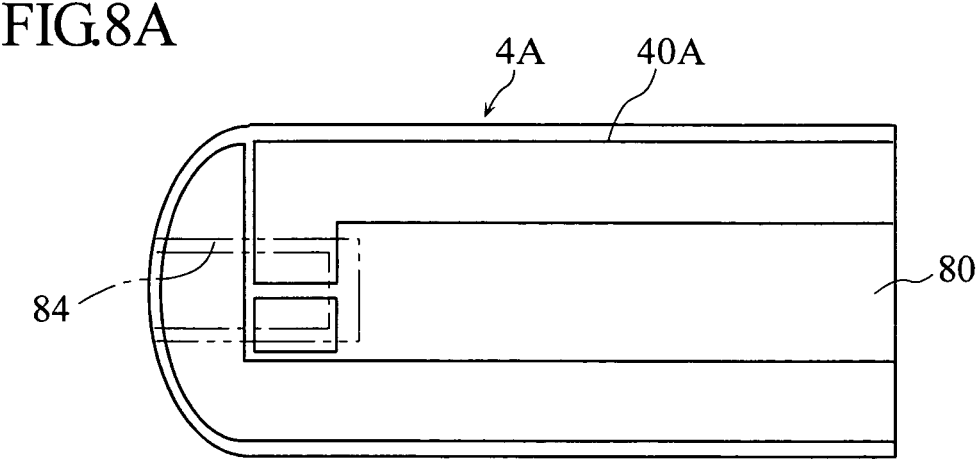
FIG. 8 includes a plan view showing other examples of biosensor according to the present invention in a state in which a cover and a spacer are removed.
Figure 8B:
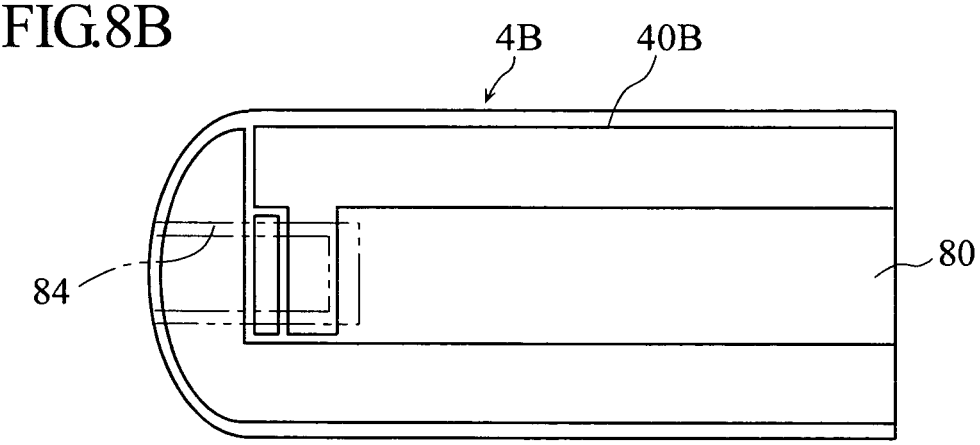
Figure 8C:
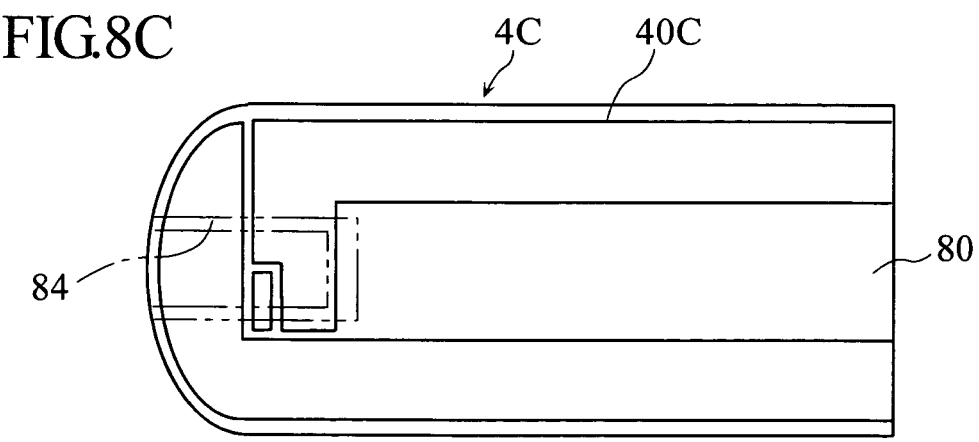
Figure 9:
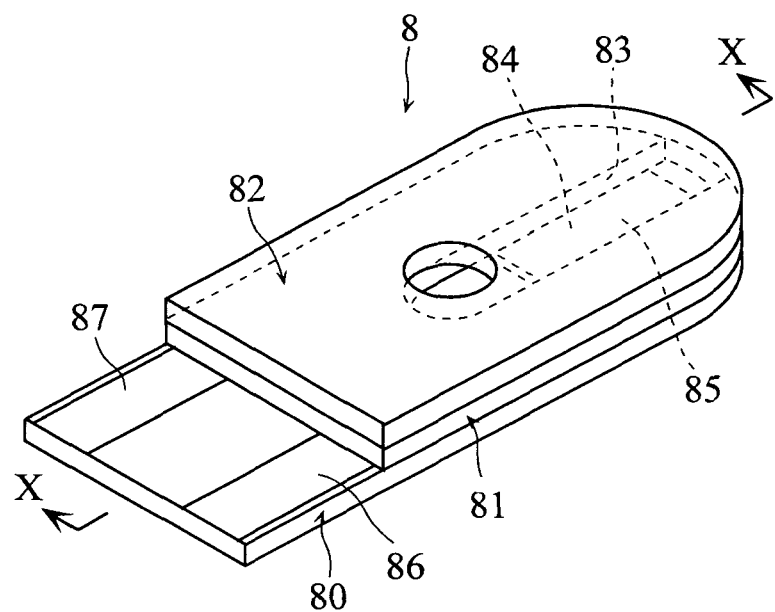
FIG. 9 is an overall perspective view showing an example of conventional biosensor.
Figure 10:
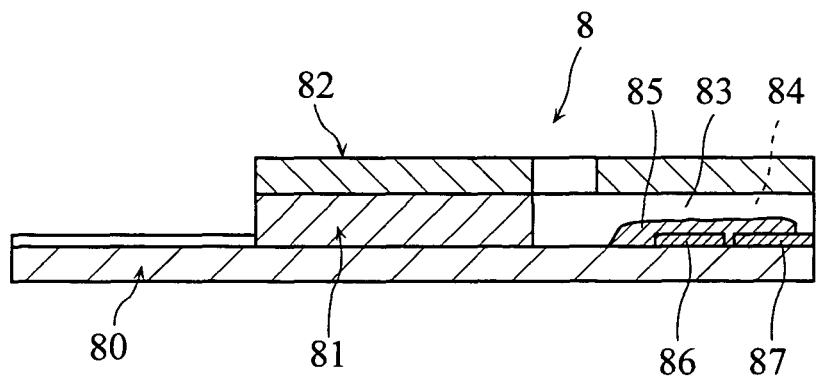
FIG. 10 is a sectional view taken along lines X-X in FIG. 9.
Figure 11:
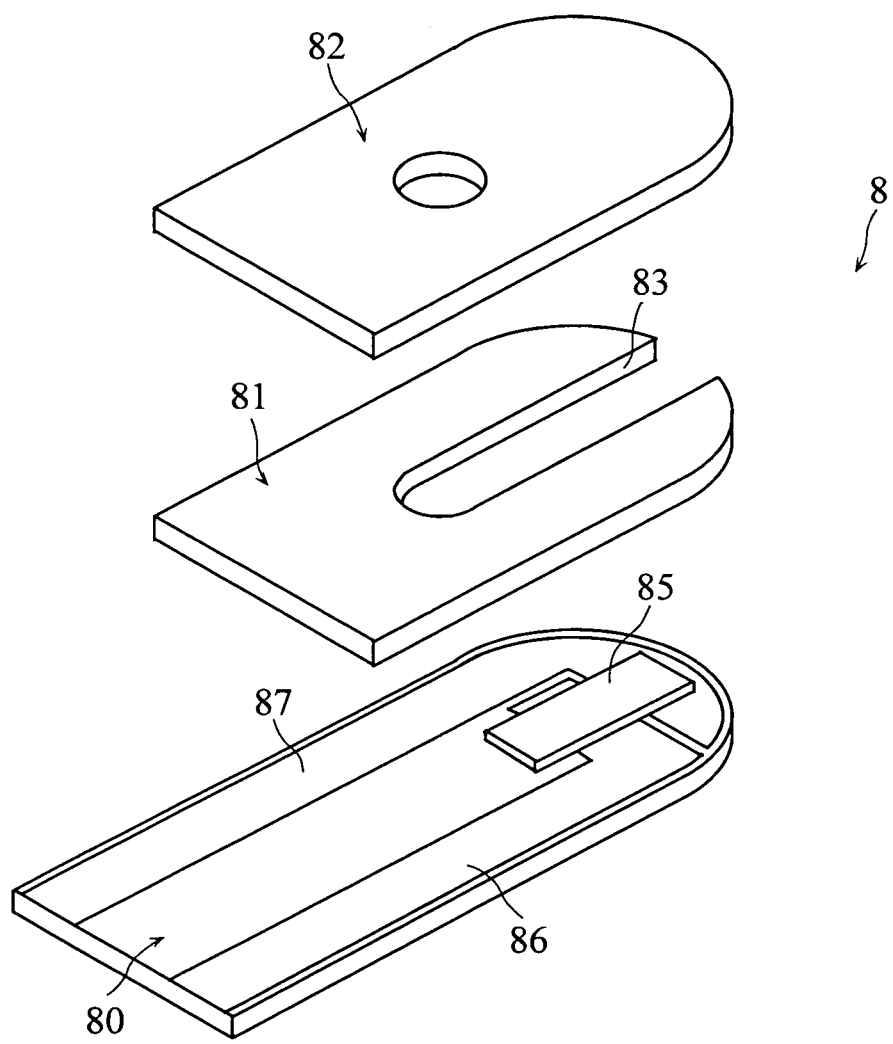
FIG. 11 is an exploded perspective view of the biosensor shown in FIG. 9.
Figure 12:
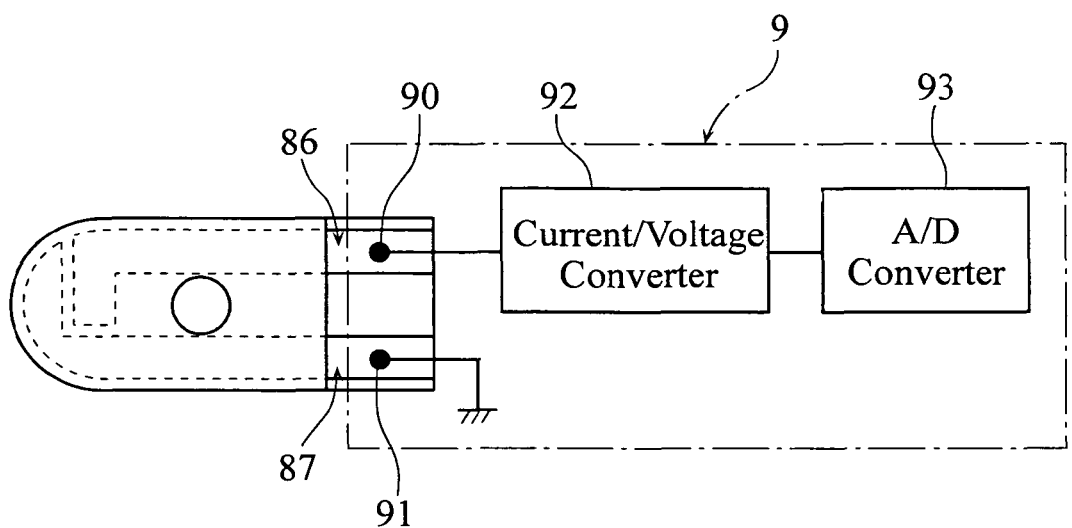
FIG. 12 shows the biosensor of FIG. 9 in a state mounted to a blood glucose level measuring apparatus, in which the analytical apparatus is illustrated in a block diagram, whereas the biosensor is illustrated in a plan view.
Figure 13:
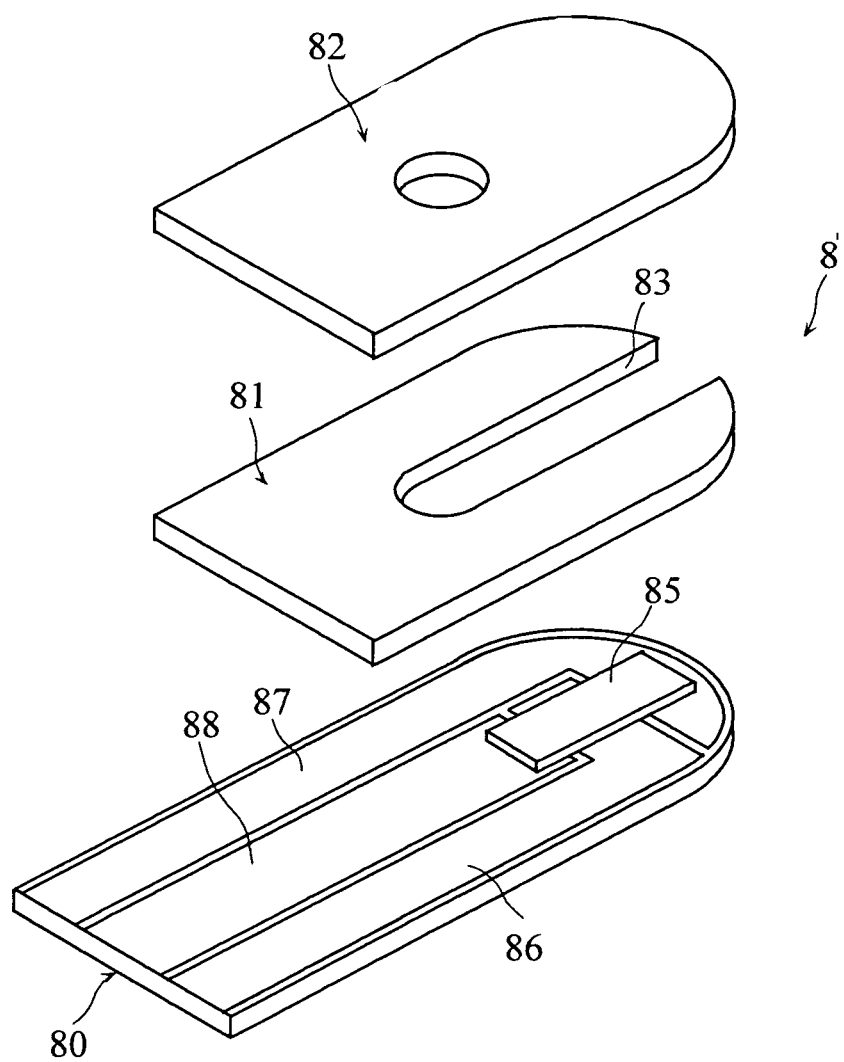
FIG. 13 is an exploded perspective view of another example of conventional biosensor.
Figure 14:
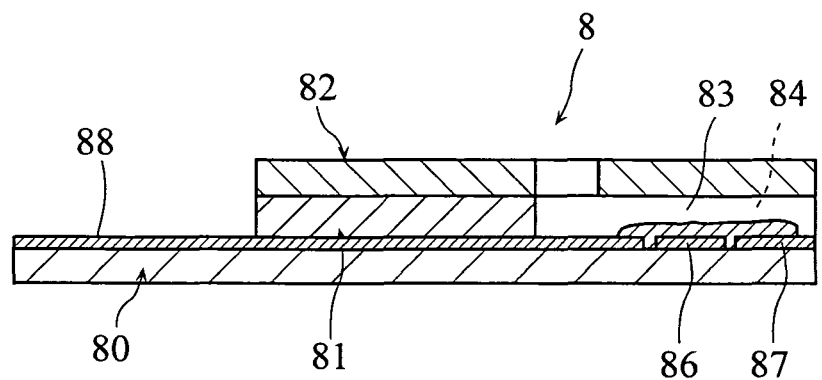
FIG. 14 is a sectional view corresponding to FIG. 10, showing the biosensor of FIG. 13.
Figure 15:
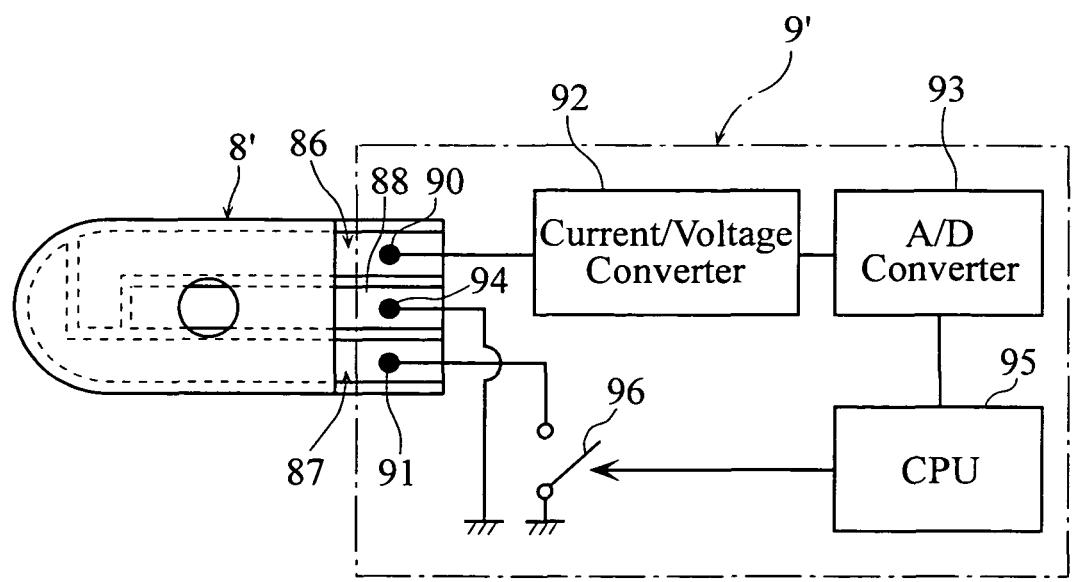
FIG. 15 shows the biosensor of FIG. 13 in a state mounted to a blood glucose level measuring apparatus, in which the analytical apparatus is illustrated in a block diagram, whereas the biosensor is illustrated in a plan view.

Other examples of biosensor according to the present invention will be described below with reference to FIGS. 7A and 7B, and FIGS. 8A-8C. In FIGS. 7A and 7B, the elements which are identical or similar to those of the biosensor 1 described above with reference to FIGS. 1-3 are designated by the same reference signs as those used for the biosensor 1. In FIGS. 8A-8C, the elements which are identical or similar to those of the biosensor 8 described with reference to FIGS. 10-12 are designated by the same reference signs as those used for the biosensor 8.

In the biosensor 3A shown in FIG. 7A, the counter electrode 30A has a structure obtained by dividing the counter electrode of the foregoing biosensor 1 (see FIGS. 1-3) at a portion on a deeper side of the capillary 13 along the direction (widthwise direction of the substrate 10) crossing the blood flow direction (longitudinal direction of the substrate 10). Thus, in this biosensor, the active portions 31A and 32A are arranged along the longitudinal direction of the substrate 10. In the biosensor 3B shown in FIG. 7B, the counter electrode 30B is divided within the capillary 13 in both of the blood flow direction (longitudinal direction of the substrate 10) and the direction (widthwise direction of the substrate 10) crossing the blood flow direction.

The biosensors 4A, 4B, 4C shown in FIGS. 8A-8C include working electrodes 40A, 40B, 40C having a shape obtained by dividing the working electrode of the conventional biosensor 8 (see FIGS. 10-12) within the capillary 84. Specifically, in the biosensor shown in FIG. 8A, the working electrode 40A is divided along the blood flow direction (longitudinal direction of the substrate 80). In the biosensor shown in FIG. 8B, the working electrode 40B is divided along the direction (widthwise direction of the substrate 80) crossing the blood flow direction (longitudinal direction of the substrate 80). In the biosensor shown in FIG. 8C, the working electrode 40C is divided along both of the blood flow direction (longitudinal direction of the substrate 80) and the direction (widthwise direction of the substrate 80) crossing the blood flow direction.

The manner of dividing part of the working electrode and the counter electrode is not limited to the examples shown in FIGS. 1-3, 7 and 8. For instance, the electrodes may be divided by a slit obliquely crossing the blood flow direction or a nonlinear slit such as a curved slit.

The application of the method of detecting blood supply lack according to the present invention, i.e., detection based on the presence or absence of the peak of the time course of the response current or the behavior of the response current after the lapse of a predetermined period from the blood introduction (i.e., whether or not the response current monotonically decreases) is not limited to a biosensor in which the working electrode or the counter electrode is divided. The method is also applicable to the blood glucose level measurement using a conventional biosensor including a working electrode or a counter electrode which is not divided (see FIGS. 10-12). In this case, when a peak is detected again after the detection of a peak (i.e., when the time course is like that schematically indicated by the double-dashed line in FIG. 6), it may be determined that the ejection of blood has occurred.

The present invention is not limited to an analytical tool in which the working electrode and the counter electrode are arranged on a common surface. For instance, the present invention is also applicable to an analytical tool in which the working electrode and the counter electrode are spaced from each other in the thickness direction. In this case, both of the working electrode and the counter electrode may be divided within the capillary.

The present invention is not only applicable to an analytical apparatus which uses a biosensor for measuring a blood glucose level but also applicable to an analytical apparatus which uses other analytical tools. For instance, the present invention is also applicable to an analytical tool designed to measure a component other than glucose in blood (e.g. lactic acid or cholesterol) or an analytical tool designed to analyze a sample other than blood.

The invention claimed is:

1. An analytical tool comprising a flow path for moving a sample introduced through a sample introduction port, and a working electrode and a counter electrode for applying a voltage to the sample supplied to the flow path, each of the working electrode and the counter electrode including a contact end for external connection to an analytical apparatus and an active region for coming into contact with the sample;

wherein the active region of one of the working electrode and the counter electrode includes a first active portion and a second active portion divided within the flow path, the first and second active portions of said one electrode being located farther from the sample introduction port than the active region of the other of the working electrode and the counter electrode;

wherein the second active portion of said one electrode is electrically separated from the first active portion of said one electrode and from the active portion of said other electrode without supply of the sample, the first active portion and the second active portion being electrically connected to each other only via a liquid junction formed by the sample for common electrical connection to the contact end of said one electrode; and wherein said one electrode includes an additional active portion located closer to the sample introduction port than the first and second active portions of said one electrode, the additional active portion of said one electrode being electrically connected to the second active portion of said one electrode without supply of the sample, the additional active portion of said one electrode being electrically separated from the first active portion and contact end of said one electrode without supply of the sample.

2. The analytical tool according to claim 1, wherein said one electrode includes a first electrode portion which includes the contact end and the first active portion, and a second electrode portion which includes the second active portion.

3. The analytical tool according to claim 1, wherein the first active portion and the second active portion are arranged along a direction crossing a sample flow direction in the flow path.

4. The analytical tool according to claim 1, wherein said one electrode is a counter electrode that includes said additional active portion for coming into contact with the sample; and wherein the active region of the working electrode is arranged downstream from the additional active portion along a sample flow direction in the flow path, and the first and second active portions of the counter electrode are arranged downstream from the active region of the working electrode along the sample flow direction in the flow path.

5. The analytical tool according to claim 4, further comprising a reagent layer continuously covering the additional active portion, the active region of the working electrode and the active region of the counter electrode and containing an electron mediator.

6. The analytical tool according to claim 1, further comprising a reagent layer continuously covering the active region of the working electrode and the active region of the counter electrode and containing an electron mediator.

7. The analytical tool according to claim 1, wherein the flow path is configured to move the sample by capillary action.

8. An analytical tool comprising a flow path for moving a sample introduced through a sample introduction port, and a working electrode and a counter electrode for applying a voltage to the sample supplied to the flow path, each of the working electrode and the counter electrode including an active region for coming into contact with the sample, the working electrode including a first contact end for external connection to an analytical apparatus, the counter electrode including a second contact end for external connection to the analytical apparatus;

wherein the active region of the counter electrode includes a first active portion and a second active portion divided within the flow path, the first and second active portions of the counter electrode being located farther from the sample introduction port than the active region of the working electrode;

wherein the second active portion of the counter electrode is electrically separated from the first active portion of the counter electrode and from the active portion of the working electrode without supply of the sample, the first active portion and the second active portion being electrically connected to each other only via a liquid junction formed by the sample for common electrical connection to the second contact end of the counter electrode; and wherein the counter electrode includes an additional active portion located closer to the sample introduction port than the first and second active portions of said one electrode, the additional active portion of the counter electrode being electrically connected to the second active portion of the counter electrode without supply of the sample, the additional active portion of the counter electrode being electrically separated from the first active portion and contact end of the counter electrode without supply of the sample.

9. An analytical tool comprising a flow path for moving a sample introduced through a sample introduction port, and a working electrode and a counter electrode for applying a voltage to the sample supplied to the flow path, each of the working electrode and the counter electrode including a contact end for external connection to an analytical apparatus and an active region for coming into contact with the sample;

wherein the active region of one of the working electrode and the counter electrode includes a first active portion and a second active portion divided within the flow path by a slit that is elongate in a flow direction of the sample, the first and second active portions of said one electrode being located farther from the sample introduction port than the active region of the other of the working electrode and the counter electrode;

wherein the second active portion of said one electrode is electrically separated from the first active portion of said one electrode and from the active portion of said other electrode without supply of the sample, the first active portion and the second active portion being electrically connected to each other only via a liquid junction formed by the sample for common electrical connection to the contact end of said one electrode; and wherein the analytical tool incorporates no additional electrode other than the counter electrode and the working electrode for detecting sufficiency of sample supply.

* * * * *